(12) United States Patent
Donovan et al.

(10) Patent No.: US 6,294,649 B1
(45) Date of Patent: Sep. 25, 2001

(54) METHOD OF CELL INHIBITION USING POLYPEPTIDES DERIVED FROM THE VENOM OF THE AUSTRIALIAN JUMPER ANT *MYRMECIA PILOSULA*

(75) Inventors: Gregory Donovan, Berowra Heights; Brian Baldo, Pymble, both of (AU)

(73) Assignee: Northern Sydney Area Health Service, St Leonards (AU)

( * ) Notice: Subject to any disclaimer, the term of this patent is extended or adjusted under 35 U.S.C. 154(b) by 0 days.

(21) Appl. No.: 09/269,229

(22) PCT Filed: Sep. 23, 1997

(86) PCT No.: PCT/AU97/00626

§ 371 Date: Oct. 8, 1999

§ 102(e) Date: Oct. 8, 1999

(87) PCT Pub. No.: WO98/13379

PCT Pub. Date: Apr. 2, 1998

(30) Foreign Application Priority Data

Sep. 23, 1996 (AU) .................................................. PO 2559

(51) Int. Cl.$^7$ .................................................. A61K 38/16
(52) U.S. Cl. ........................... 530/324; 530/326; 514/12; 514/13
(58) Field of Search .................................. 530/326, 329; 514/13, 12

(56) References Cited

U.S. PATENT DOCUMENTS

| | | | | |
|---|---|---|---|---|
| 4,883,661 | * | 11/1989 | Daly | 424/85.2 |
| 5,576,351 | * | 11/1996 | Yoshimura | 514/665 |
| 5,604,244 | * | 2/1997 | DeSantis | 514/317 |
| 5,668,112 | * | 9/1997 | Lipsky | 514/19 |
| 5,766,873 | * | 6/1998 | Noble | 435/25 |
| 5,858,365 | * | 2/1999 | Faller | 424/184.1 |

OTHER PUBLICATIONS

Donovan, Biochimica et Biophysica Acta 1171 272–280, 1993.*

Biochemistry and Molecular Biology International, vol. 39, No. 5, Aug. 1996. Donovan, Gregory et al., "Expression of Jumper Ant (*Myrmecia Pilosula*) venom allergens: posttransational processing of allergen gene products.", pp. 877–885.

Electrophoresis, vol. 16, No. 5, May 1995. Donovan, Gregory et al., "Separation of jumper ant (*Murmecia pilosula*) venom allergens: A novel group of highly basic proteins.", pp. 804–810.

* cited by examiner

Primary Examiner—Christopher S. F. Low
Assistant Examiner—David Lukton
(74) Attorney, Agent, or Firm—Browdy and Neimark

(57) ABSTRACT

An isolated polypeptide having cytotoxic activity comprising the amino acid sequence of Pilosulin 1 shown in the figure, and active portion thereof, or a functionally equivalent amino acid sequence thereof, and a method of inhibiting the growth of a cell comprising exposing the cell to an effective amount of Pilosulin 1 shown in the figure, and active portion thereof, or a functionally equivalent amino acid sequence thereof, such that the growth of the cell is inhibited.

4 Claims, 5 Drawing Sheets

```
Gly Leu Gly Ser Val Phe Gly Arg Leu Ala Arg Ile Leu Gly Arg
1            5                10                   15

Val Ile Pro Lys Val Ala Lys Lys Leu Gly Pro Lys Val Ala Lys
                20                25                   30

Val Leu Pro Lys Val Met Lys Glu Ala Ile Pro Met Ala Val Glu
                35                40                   45

Met Ala Lys Ser Gln Glu Glu Gln Gln Pro Gln
                50                55
```

METHOD OF CELL INHIBITION USING POLYPEPTIDES DERIVED FROM THE VENOM OF THE AUSTRIALIAN JUMPER ANT *MYRMECIA PILOSULA*

TECHNICAL FIELD

The invention relates to polypeptides having cytotoxic activity, methods of inhibiting cells, and in particular to methods of inhibiting cells using polypeptides derived from ant venom.

BACKGROUND ART

The present inventors reported the molecular cloning and characterisation of a major allergen from the venom of the Australian jumper ant Myrmecia pilosula. The results of this work was reported in Donovan et al. 1993 Biochemica et Biophysica Acta, 1171: 272–280. This major allergen was originally called Myr p I.

Since the report on this major allergen from Myrmecia pilosula, the present inventors have made the surprising discovery that several peptides derived from the Myr p I amino acid sequence, including a polypeptide called Pilosulin 1, have potent cytotoxic activity to a wide range of cells.

DISCLOSURE OF THE INVENTION

In a first aspect, the present invention consists in an isolated polypeptide having cytotoxic activity comprising the amino acid sequence of Pilosulin 1 shown in FIG. 1 from residues 1 to 56, an active portion thereof. or a functionally equivalent amino acid sequence thereof.

Preferably, the polypeptide is Pilosulin 1, an active portion thereof, or a functionally equivalent amino acid sequence thereof. More preferably the polypeptide is Pilosulin 1.

In a second aspect, the present invention consists in an isolated polypeptide having cytotoxic activity comprising the amino acid sequence from residues 1 to 22 (SEQ ID NO:2) shown in FIG. 1, an active portion thereof, or a functionally equivalent amino acid sequence thereof.

In one preferred form, the polypeptide includes the amino acid sequence from residues 1 to 22 (SEQ ID NO:2) shown in FIG. 1.

As used herein the term "functionally equivalent amino acid sequence" is intended to cover minor variations in the amino acid sequence described which results in a polypeptide having relative cytotoxic activity which is not substantially less than that of the corresponding native polypeptide. Preferably, a polypeptide having ail altered amino acid sequence from its sequence shown in FIG. 1 has substantially the same or greater cytotoxic activity than that of the native polypeptide. This may be achieved by various changes in the sequence, such as insertions, deletions and substitutions.

Polypeptides including the amino acids from residues 1 to 22 (SEQ ID NO:2) shown in FIG. 1, or Pilosulin 1, or active portions thereof, or functionally equivalent amino acid sequences thereof, can be produced recombinantly or produced synthetically by standard methods known to the art. Furthermore, modifications of the polypeptides can be carried out by known techniques after production of the polypeptides.

It will also be appreciated that the polypeptides of the present invention may have at least some of the peptide bonds between the amino acids replaced by peptide bond mimics (mimetics) to form pseudopeptide analogues. Such mimics are well known to the art and include N-methyl isosteres, hydroxyl isosteres, reduced peptide bonds and retro-inverso-peptomimetics. Alterations of the peptides in this manner may reduce or eliminate their antigenicity so as to reduce the chance of stimulating the immune response in subjects when administered with the peptides over a prolonged period.

In a third aspect, the present invention consists in a method of inhibiting the growth of a cell comprising exposing the cell to an effective amount of a polypeptide according to the first or second aspects of the present invention.

It will be appreciated that the method according to the present invention is suitable to inhibit any cell type sensitive to the inhibitory or cytotoxic action of polypeptides according to the present invention including the amino acid sequence from residues 1 to 22 (SEQ ID NO:2) shown in FIG. 1, or Pilosulin 1, an active portion thereof, or functionally equivalent amino acid sequence thereof.

Preferably the cell is a tumour cell, a cancer cell, a B-lymphocyte or a T-lymphocyte.

The effective amount of the cytotoxic polypeptides according to the present invention will often depend on the cell type being inhibited. Concentrations of Pilosulin 1, for example, of approximately 0.02 $\mu$M have been found to inhibit cells but lower concentrations of other polypeptides may also be suitable to inhibit certain cell types. In one preferred form, concentrations of at least about 0.2 $\mu$M, preferably at least about 2 $\mu$M, of the peptides according to the present invention are used to inhibit the growth of cells.

Preferably, the inhibition causes cell death.

Polypeptides including the amino acid sequence from residues 1 to 22 (SEQ ID NO:2) shown in FIG. 1, or Pilosulin 1, or active portions thereof, or functionally equivalent amino acid sequences thereof, may be used to inhibit cells in vitro, for example in laboratory applications, or in vivo, for example, by administration to a subject.

The method according to the third aspect of the present invention may be carried out by administering the active polypeptide to a subject by any known delivery method or system. For example, the delivery may be topically, parentally or via the alimentary canal.

In a fourth aspect, the present invention consists in a composition for use in inhibiting the growth of a cell, the composition comprising a polypeptide according to the first or second aspects of the present invention, together with a pharmaceutically acceptable diluent.

In order that the present invention may be more clearly understood, preferred forms will be described with reference to the following examples and figures.

BRIEF DESCRIPTION OF THE DRAWINGS

FIG. 1 shows the amino acid sequence of the polypeptide called Pilosulin 1 derived from ant venom; (SEQ ID NO: 1)

FIG. 5 shows results of kinetics of Pilosulin 1 T-cell killing at various temperatures.

MODES FOR CARRYING OUT THE INVENTION

Pilosulin 1 Sequence

FIG. 1 shows that the amino acid sequence of Pilosulin 1 which comprises a 56 amino acid residue polypeptide sequence. The partial sequence of Pilosulin 1 from residues 12 to 56 has substantially reduced cytotoxicity to cells and the partial polypeptide 23 to 56 has no detectable cytotoxicity to cells tested. This suggests a possible cytotoxic moiety between residues 1 to 22. Pilosulin 1 is cytotoxic for proliferating Epstein-Barr Virus transformed B-cells and also for some solid tumour cell lines including a breast cancer, a brain tumour and a kidney cell tumour line. Pilostilin 1 is also cytotoxic for normal blood cells, in particular, lymphocytes monocytes and natural killer cells but granulocytes are resistant.

Cell proliferation and flow cytometry have been used to determine the cytotoxic effects on cells. Cell proliferation involves growing cells to log-phase growth and adding Pilosulin 1 at different final peptide concentrations and $^3$H-methyl thymidine at the same time. The cells are incubated at 37° C. for 16 hours, harvested, lysed and washed and the cells liquid scintillation counted. Flow cytometry employs the exclusion of propidium iodide from cells as an index of their viability. In experiments where fluorescent labelled monoclonal antibodies recognising cell specific markers were used, exclusion of 7-actinomycin D was used as the index of cell viability. In these latter experiments cells were incubated with the fluorescent antibodies and then washed to remove unbound antibodies. The treated cells were stored on ice and Pilosulin 1 added 5 minutes prior to flow cytometric measurement.

Pilosulin 1 Cytotoxicity (1) Red Blood Cell Lysis.

Figure 3:
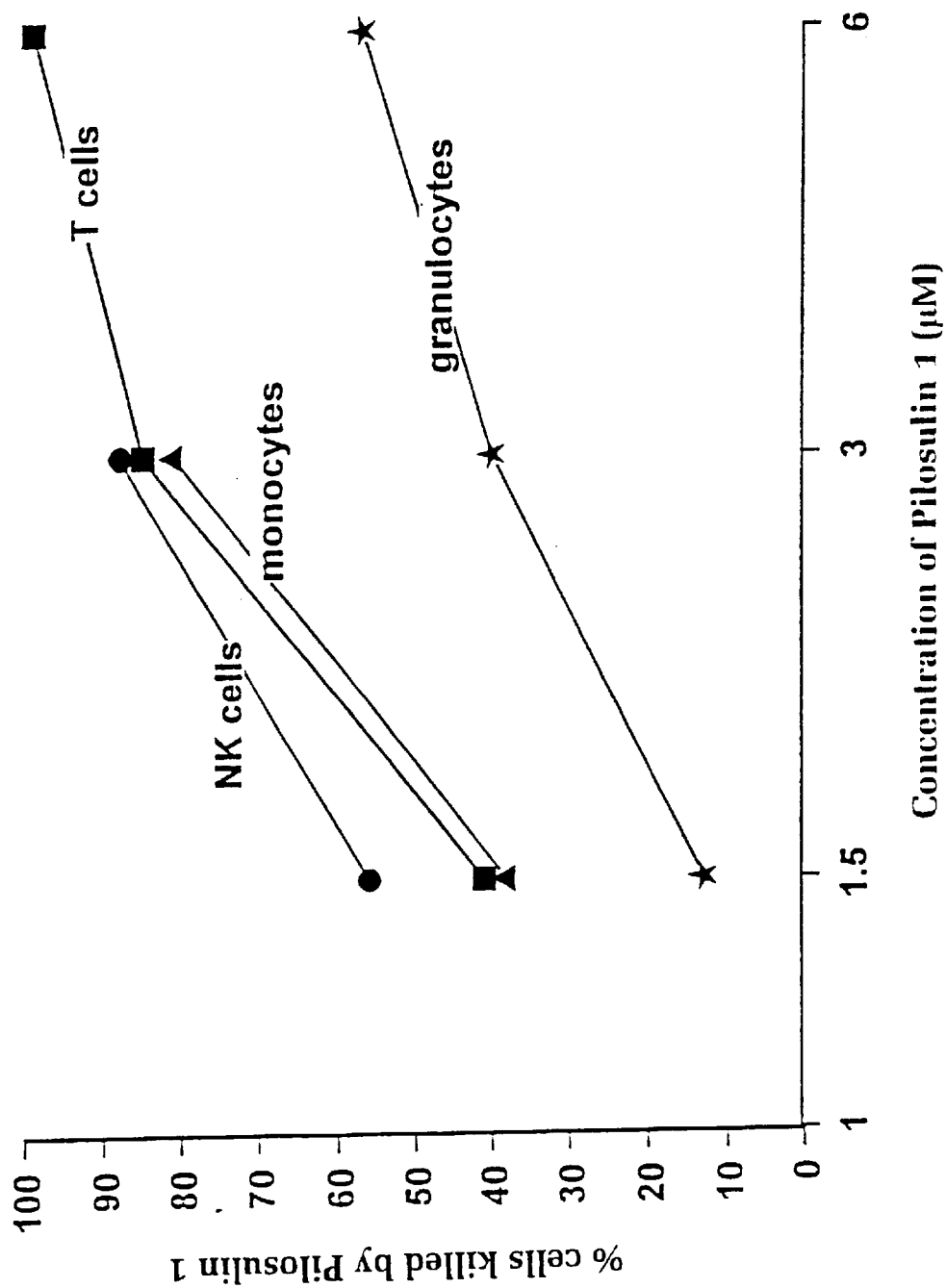
FIG. 3 shows the results of an inhibition assay of Pilosulin 1 against various blood cell types.

Red blood cells were prepared from fresh whole blood. Red blood cells were diluted to 1% (v/v) with PBS and 0.1 mL aliquots added to a 96 well microtitre plate. Venom and venom peptides were added in 5 μL of normal saline. Whole ant venom concentration (final): 80, 40, 20, 10, 5, 2.5, 1.25, 0.625, 0.3125 4μg/mL. Venom peptide concentration (final): 80, 40, 20, 10, 5, 2.5, 1.25, 0.625, 0.3125 μM. The results are shown in FIG. 3. The results indicate that the bee venom cytotoxin melittin was most efficient on a molar basis in the lysis of red blood cells.

(2) Cell proliferation studies.

Figure 2:
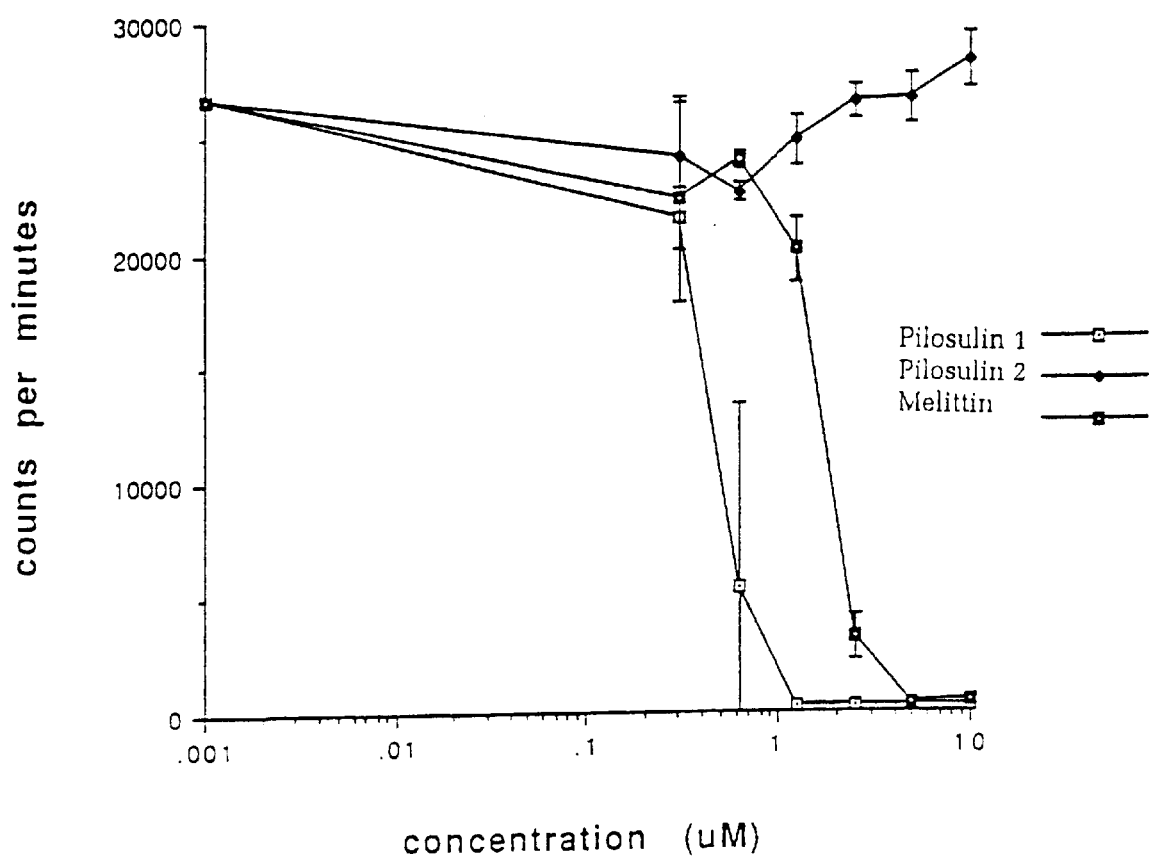
FIG. 2 shows the results of an Epstein-Barr Virus transformed B-cells inhibition assay of Pilosulin 1, Pilosulin 2, and melittin.

Epstein Barr-transformed human B-cells grown to log phase. One hundred mL of cells ($10^5$ cells) were placed in the wells of microtitre plates. Venom and venom peptides added to the wells in 5 mL to give final concentrations used in the red cell lysis experiment. One μCi of $^3$H-methyl-thymidine was added to the wells and the plates incubated overnight at 37° C. Cells harvested 17 hr later and counted. Results are shown in FIG. 2. Data suggests that Pilosulin 1 is approximately 4-times more effective as a cytotoxini at 50% cell viability.

(3) Flow Cytometry

Flow cytometry can measure cell viability by their ability to exclude a fluorescent dye such as propidium iodide or 7-actinomycin D. EBV-transformed B-cells were cultured to log-phase growth and venom and venom peptides added. Typically, a proportion of the untreated control cells (usually about 15%) were permeable to propidium iodide. This value represented the control value. Cells were treated for 5 minutes with Pilosulin 1, Pilosulin 2 and melittin over a concentration range of 0.1 to 10 μM and then cell numbers were measured in the flow cytometer. The results are shown in Table 1.

TABLE 1

| Cytotoxic peptide | Concentration | % Viable Cells |
|---|---|---|
| JA Venom | 10 μg/mL | 16.1 |
| Melittin | 5 μM | 53.5 |
| Pilosulin 1 | 5 μM | 16.2 |
| peptide 1* (residues 11–56) | 5 μM | 65.2 |
| peptide 2 (residues 23–56) | 5 μM | 85.0 |
| peptide 3 (residues 31–56) | 5 μM | 84.4 |
| peptide 4 (residues 37–56) | 5 μM | 84.3 |
| peptide 5 (residues 45–56) | 5 μM | 84.2 |

*see FIG. 1

This data confirms the proliferation data and also suggests that a cytotoxic moiety might exist in the first 22 or so residues of Pilosulin 1.

The relative cytotoxicity of Pilosulin 1 for the different components of the leucocyte population was studied and the results are shown in FIG. 3. The assay was carried out by first labelling a leucocyte preparation with fluorescent antibodies that identify cell-specific markers, briefly treating the cells with Pilosulin 1 and then measuring the cell viability in the flow cytometer byr uptake of 7-actinomycin D. Preliminary indications are that Pilosulin 1 has differential toxicity, the lymphocyte population being completely killed at 5 μM whereas the granulocyte population appears relatively unaffected.

(4) Cell Viability Studies

Figure 4:
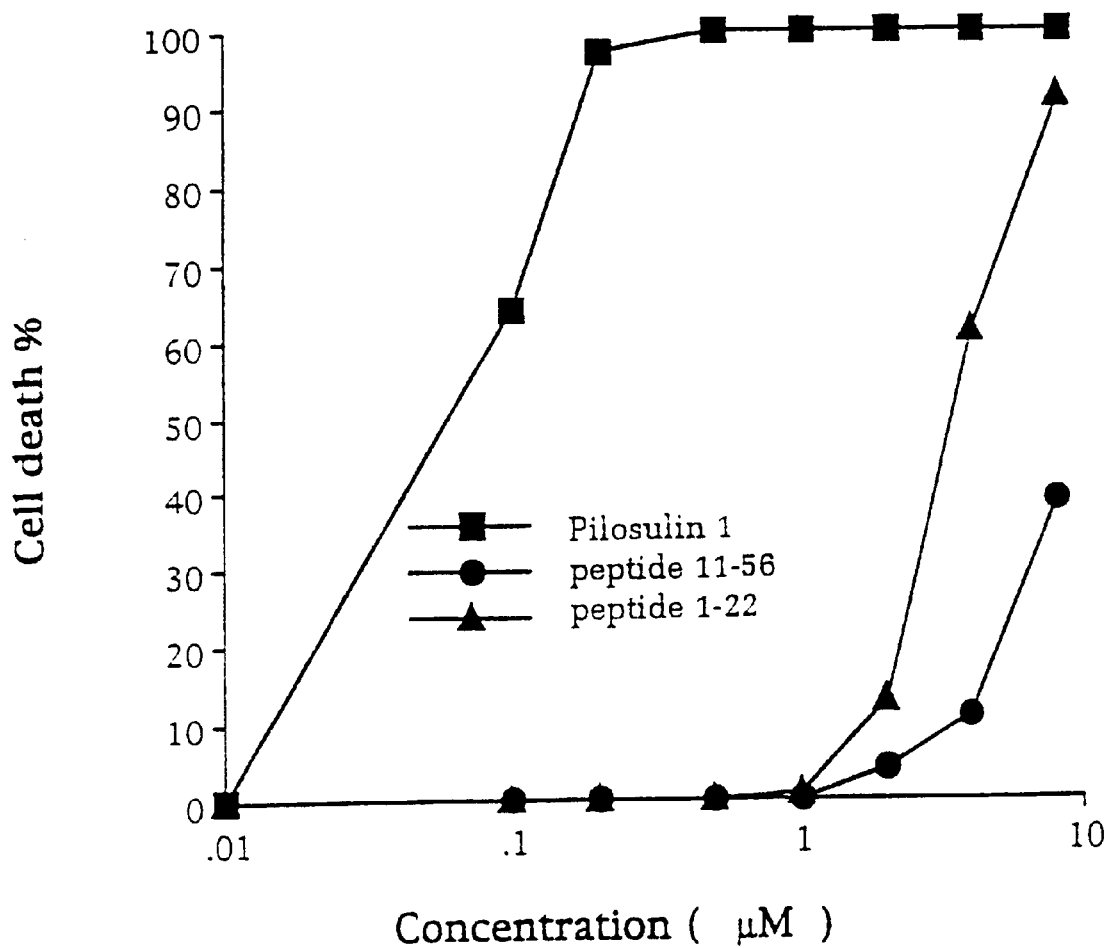
FIG. 4 shows the effect of some peptides according to the present invention on the viability of Epstein Barr-transformed B-cells (EBV B-cells)

The effect of Pilosulin 1, peptide (1-22) (SEQ ID NO:2) and peptide (11-56) on the viability of EBV B-cells was investigated. Log-phase EBV B-cells (2×10$^5$) were incubated for 10 min in the presence of various peptides and 7 aminoactinomycin D (7-AAD) (4 μg/mL). Uptake of 7-AAD was measured by flow cytometry where non-viable cells take up 7-AAD. The results are shown in FIG. 4.

Pilosulin 1. at a concentration of 0.1 μM. killed more than 60% of cells and concentrations of greater than 0.2 μM killed all cells. The next most potent peptide tested was peptide 1-22 which killed more than 60% of cells at a concentration of 5 μM. A concentration of 10 μM of peptide 1-22 killed nearly all cells. Peptide 11-22 was slightly less active killing about 50% of cells at a concentration of 10 μM.

(5) Kinetics

Figure 5:
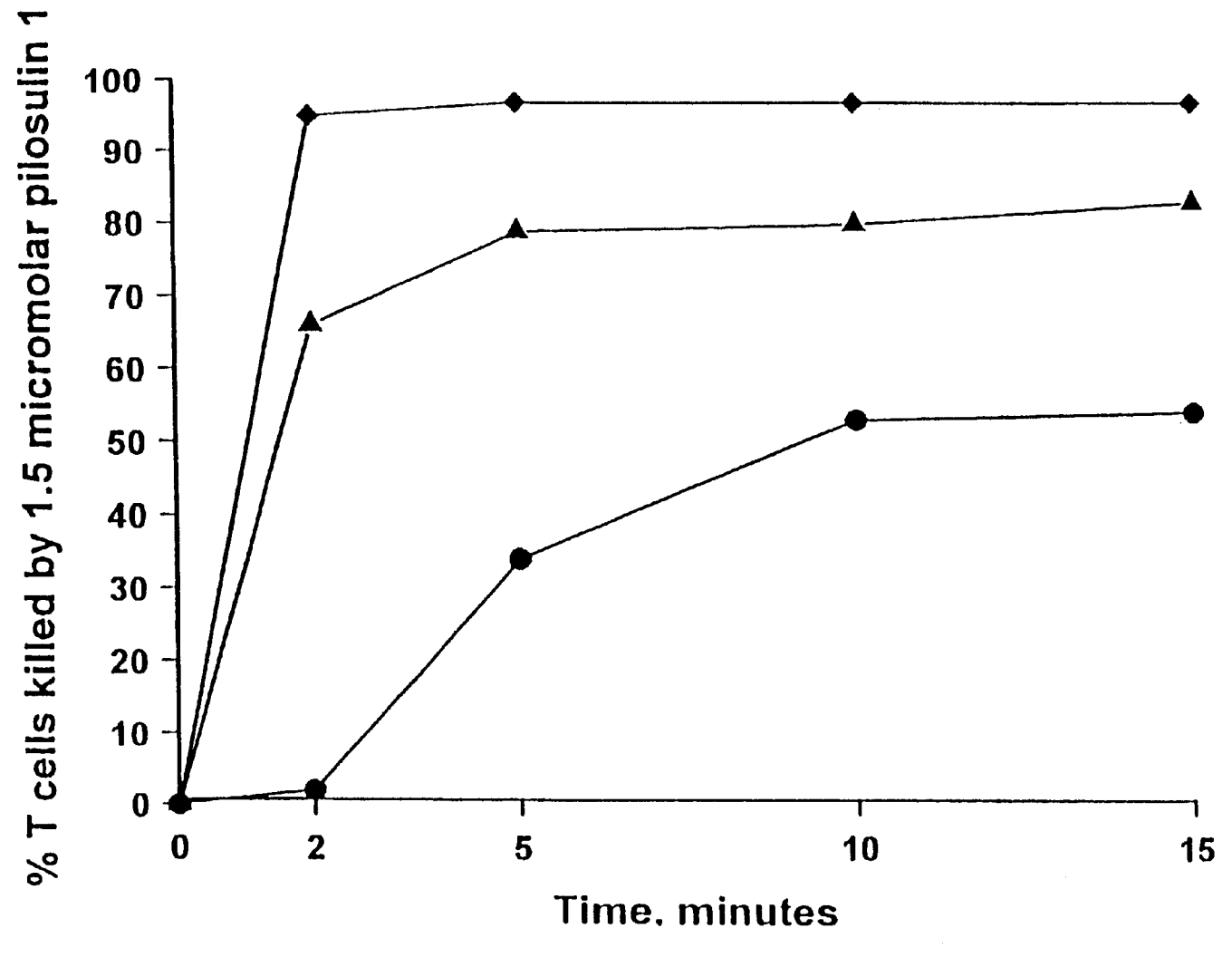

The kinetics of Pilosulin 1 and melittin cell killing at different temperatures were investigated. Antibody-labelled (CD3-FITC) white blood cells were incubated with 7-AAD (4 μg/mL) and either 1.5 μM Pilosulin 1 or 3 μM melittin. Three tubes were prepared for each peptide and the tubes were incubated at either 0° C. (circles), room temperature (triangles), or 37° C. (diamonds). Samples of each tube were analysed on a flow cytometer at time zero and thereafter at 2, 5 10 and 15 minutes. The results for Pilosulin 1 are shown in FIG. 5.

At 37° C., similar results were observed for both Pilosulin 1 and melittin where all cells were killed at 2 minutes. At room temperature, 65% and 85% respectively of cells were killed at 2 minutes by Pilosulin 1 and melittin. Eighty percent of cells were killed by Pilosulin 1 at 5 minutes at room temperature and further incubation had no further effect on the remaining viable cells. In contrast, melittin killed all cells at 5 minutes when incubated at room temperature. Fifty percent of cells were killed at 10 minutes at 0° C. by Pilosulin 1 whereas only 25% of cells were killed at this time and temperature by melittin These results may suggest that different killing mechanisms may be involved by these two cytotoxins.

Uses of Pilosulin 1

The use of cytotoxic peptides coupled to antibodies recognising tumour specific antigens as cancer therapeutic reagents has received new impetus with the development of recombinant DNA methods to manufacture small antibody components called single chain Fv antibodies (scFvs) having identical specificities to the native antibodies. The recombinant DNA technology has also greatly facilitated the screening for tumour specific antibodies. Pilosulin 1 is highly cytotoxic and is a good candidate for use in recombinant antibody preparations. Pilosulin 1 has been cloned into DNA vectors by the present inventors and therefore it can be further cloned into scFv molecules. There is some evidence to indicate that only a small part of the Pilosulin 1 peptide may be required for its cytotoxic activity and this smaller portion could yield an equally cytotoxic recombinant polypeptide.

Pilosulin 1 has potent cytotoxicity towards a number of different cancer cells and in particular to rapidly dividing cancer cells of myeloid and lymphoid origin. Its cytotoxicity for normal blood cells is low and therefore is a suitable candidate to remove lymphocytes from blood without killing many of the other cell populations in blood. A particularly good use for Pilosulin 1 may be in bone marrow graft procedures where the patient's lymphocytes must be removed before cell replacement.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An isolated cytotoxic peptide, consisting of SEQ ID NO:2.

2. A composition comprising a peptide according to claim 1, together with an acceptable diluent, wherein the peptide is present in an amount effective to inhibit growth of a cell.

3. A method of inhibiting the growth of a cell comprising contacting the cell with a peptide of SEQ ID NO: 1 for a time and under conditions effective to inhibit growth of the cell.

4. The method of claim 3 wherein the cell is selected from the group consisting of a tumor cell, a cancer cell, a B-lymphocyte, and a T-lymphocyte.

* * * * *

SEQUENCE LISTING

```
<160> NUMBER OF SEQ ID NOS: 2

<210> SEQ ID NO 1
<211> LENGTH: 56
<212> TYPE: PRT
<213> ORGANISM: Myrmecia pilosula

<400> SEQUENCE: 1

Gly Leu Gly Ser Val Phe Gly Arg Leu Ala Arg Ile Leu Gly Arg Val
1               5                   10                  15

Ile Pro Lys Val Ala Lys Lys Leu Gly Pro Lys Val Ala Lys Val Leu
            20                  25                  30

Pro Lys Val Met Lys Glu Ala Ile Pro Met Ala Val Glu Met Ala Lys
        35                  40                  45

Ser Gln Glu Glu Gln Gln Pro Gln
    50                  55

<210> SEQ ID NO 2
<211> LENGTH: 22
<212> TYPE: PRT
<213> ORGANISM: Myrmecia pilosula

<400> SEQUENCE: 2

Gly Leu Gly Ser Val Phe Gly Arg Leu Ala Arg Ile Leu Gly Arg Val
1               5                   10                  15

Ile Pro Lys Val Ala Lys
            20
```